(12) United States Patent
Massé et al.

(10) Patent No.: US 8,496,906 B2
(45) Date of Patent: Jul. 30, 2013

(54) BIOLOGICAL OXIDATION OF HYDROGEN SULPHIDE IN A PSYCHROPHILIC ANAEROBIC DIGESTION BIOREACTOR SUBJECTED TO MICROAEROBIC CONDITIONS

(75) Inventors: Daniel I. Massé, Sherbrooke (CA); Steve Boivin, Sherbrooke (CA)

(73) Assignees: Her Majesty the Queen in right of Canada as represented by the Minister of Agriculture and Agrifood, Sherbrooke (CA); Bio-Terre Systems Inc., Sherbrooke (CA)

( * ) Notice: Subject to any disclaimer, the term of this patent is extended or adjusted under 35 U.S.C. 154(b) by 0 days.

(21) Appl. No.: 13/292,732

(22) Filed: Nov. 9, 2011

(65) Prior Publication Data

US 2012/0190101 A1 Jul. 26, 2012

Related U.S. Application Data

(60) Provisional application No. 61/411,690, filed on Nov. 9, 2010.

(51) Int. Cl.
*C01B 17/04* (2006.01)
(52) U.S. Cl.
USPC ...................................... 423/573.1; 435/266
(58) Field of Classification Search
USPC ...................................... 423/573.1; 435/266
See application file for complete search history.

(56) References Cited

U.S. PATENT DOCUMENTS

| 5,863,434 | A | 1/1999 | Masséet al. |
| 6,291,232 | B1 * | 9/2001 | Miller, III ...................... 435/262 |
| 6,299,774 | B1 * | 10/2001 | Ainsworth et al. ........... 210/603 |

FOREIGN PATENT DOCUMENTS

CA 2138091 6/1996

OTHER PUBLICATIONS

Abatzoglou, N., and Boivin, S., "A review of biogas purification processes," Biofuels, Bioproducts & Biorefining. vol. 3, No. 1 pp. 42-71 (2009).
Burgess et al., "Developments in odour control and waste gas treatment biotechnology: a review," Biotechnology Advances. vol. 19, No. 1 pp. 35-63 (2001).
Janssen et al., "Removal of hydrogen sulphide from wastewater and waste gases by biological conversion to elemental sulphur: Colloidal and interfacial aspects of biologically produced sulphur particles," Colloids and Surfaces A: Physicochemical and Engineering Aspects. vol. 151, Nos. 1-2 pp. 389-397 (1999).
Jenicek et al., "Use of microaerobic conditions for the improvement of anaerobic digestion of solid wastes," Water Science & Technology, vol. 58, No. 7 pp. 1491-1496 (2008).
Jensen, A.B., and Webb, C., "Treatment of H2S-containing gases—A review of microbiological alternatives," Enzyme and Microbial Technology. vol. 17 pp. 2-10 (1995).
Masséet al., "Potential of low-temperature anaerobic digestion to address current environmental concerns on swine production," J. Anim. Sci. vol. 88 pp. E112-E120 (2009).
Notification of Transmittal of the International Search Report and the Written Opinion of the International Searching Authority, or the Declaration corresponding to International Patent Application No. PCT/CA2011/001252 dated Jan. 23, 2012.
van der Zee et al., "Sulphide removal by moderate oxygenation of anaerobic sludge environments," Bioresource Technology. vol. 98 pp. 518-524 (2007).
Cirne et al., "Control of sulphide during anaerobic treatment of S-containing wastewaters by adding limited amounts of oxygen or nitrate," Reviews in Environmental Science & Biotechnology. vol. 7, No. 2 pp. 93-105 (2008).
Grant et al., "Differential response of weed and crop species to potassium and sulphur fertilizers," Canadian Journal of Plant Science. vol. 87, No. 2 pp. 293-296 (2007).
Khanal, S.K., and Huang, J.-C., "Anaerobic Treatment of High Sulfate Wastewater with Oxygenation to Control Sulfide Toxicity," Journal of Environmental Engineering, ASCE. vol. 129, No. 12 pp. 1104-1111 (2003).
Massé, D.I., and Masse, L., "Treatment of slaughterhouse wastewater in anaerobic sequencing batch reactors," Canadian Agricultural Engineering. vol. 42, No. 3 pp. 131-137 (2000).
Schieder et al., "Microbiological removal of hydrogen sulfide from biogas by means of a separate biofilter system: experience with technical operation," Water Science and Technology. vol. 48, No. 4 pp. 209-212 (2003).
Syed et al., "Removal of hydrogen sulfide from gas streams using biological processes —A review," Canadian Biosystems Engineering. vol. 48 pp. 2.1-2.14 (2006).

* cited by examiner

*Primary Examiner* — Timothy Vanoy
(74) *Attorney, Agent, or Firm* — Jenkins, Wilson, Taylor & Hunt, P.A.

(57) ABSTRACT

A biological process for removing hydrogen sulphide from biogas is disclosed. The process involves injecting a small quantity of air into the gas phase or the liquid phase of a psychrophilic bioreactor to allow microbial flora to convert the hydrogen sulphide into elemental sulphur.

26 Claims, 10 Drawing Sheets

BIOLOGICAL OXIDATION OF HYDROGEN SULPHIDE IN A PSYCHROPHILIC ANAEROBIC DIGESTION BIOREACTOR SUBJECTED TO MICROAEROBIC CONDITIONS

CROSS-REFERENCE TO RELATED APPLICATIONS AND DOCUMENTS

This application claims priority from U.S. provisional patent application 61/411,690 filed on Nov. 9, 2010, the content of which is incorporated by reference in its entirety.

TECHNICAL FIELD

The present invention relates to a biological process for removing hydrogen sulphide from biogas.

BACKGROUND ART

During anaerobic digestion of organic substrates of agricultural, agri-food, municipal and industrial origin, renewable energy is produced in the form of biogas. Biogas contains methane, carbon dioxide and hydrogen sulphide in proportions ranging from 70% to 80%, 20% to 30%, and 0.1% to 4%, respectively. When biogas is used to produce heat or electrical energy, the presence of hydrogen sulphide in the biogas poses a major challenge. During combustion, this hydrogen sulphide is converted to sulphur oxide or sulphuric acid, which accelerates corrosion of equipment fueled by biogas, reduces its lifespan and substantially increases energy production costs. Current technologies (physical or chemical) for removing sulphur are expensive and not economically feasible at the farm scale.

On-farm methanation of agricultural waste has many environmental benefits, but also entails certain challenges in terms of adapting the technology to farm circumstances and scale. One of these challenges is the significant corrosive potential of biogas, primarily attributable to its water and hydrogen sulphide ($H_2S$) content. The sulphur oxides ($SO_2$) formed during the combustion of biogas can cause premature deterioration of biogas-fueled equipment and can also corrode structures in the vicinity of the bioreactors. In addition, after its release into the atmosphere, $SO_2$ contributes to acid rain and, consequently, to forest degradation and loss of biodiversity.

$H_2S$ is produced during anaerobic digestion (AD) of municipal, agro-industrial or agricultural waste (Shchieder et al., 2003, Water Science Technology, 48(4): 209-212). The sulphur is present in the methionine and cysteine, two essential amino acids of animal and plant metabolism. Liquid animal manure is therefore rich in sulphur and produces a biogas with $H_2S$ concentrations as high as 6000 ppm. There are many biogas purification technologies available at both the experimental and commercial stages (Abatzoglou et al., 2005, Biofuels, Bioproducts & Biorefining, 3(1): 42-71; Jensen et al., 1999. Enzyme and microbial technology, 17: 2-10), but few are adaptable to the farm scale from a technical and economical perspective. The biological route therefore has many advantages and is the main focus of research in the field of biogas purification (Burgess et al., 2001. Biotechnology advances, 19: 35-63; Syed et al., 2006, Canadian Biosystems engineering, 48: 2.1-2.14).

One of the biological processes for controlling $H_2S$ emissions is to inject a limited quantity of air into the gas phase of the AD bioreactor. Under limited oxygen ($O_2$) (microaerobic) conditions, microorganisms will promote the chemical reaction of oxidation of $H_2S$ into elemental sulphur ($S^0$). In the presence of excess oxygen, microorganisms will instead promote the production of sulphates, a reaction with a higher energy yield. See the following equations:

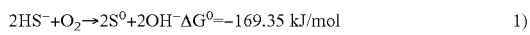

$$2HS^- + O_2 \rightarrow 2S^0 + 2OH^- \quad \Delta G^0 = -169.35 \text{ kJ/mol} \qquad 1)$$

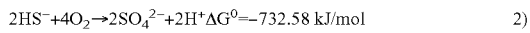

$$2HS^- + 4O_2 \rightarrow 2SO_4^{2-} + 2H^+ \quad \Delta G^0 = -732.58 \text{ kJ/mol} \qquad 2)$$

$O_2$ can be added either via the gas phase or via the liquid phase. The latter option requires a greater quantity of air, since part of the $O_2$ will be consumed for aerobic oxidation of the organic matter (Jenicek et al., 2008, Water Science& Technology, 58(7): 1491-1496). The goal is to promote the action of facultative aerobic thiobacteria, normally present in AD sludges, without however adversely affecting the anaerobic process, the purpose of which is to produce methane. In fact, too much oxygen can inhibit the strictly anaerobic bacteria (Cirne et al., 2008, Rev Environmental Science & Biotechnology, 7: 93-105).

The crystalline form of this biologically produced sulphur is different from the form normally observed with chemical methods. These white or pale yellow orthorhombic crystals ($S^8$) can be separated from the liquid fraction by sedimentation because of its higher density compared to water. Negatively charged polymer molecules are believed to bind to the $S^8$ nuclei, which give the sulphur its hydrophobic properties (Janssen et al., 1999. Colloids and Surfaces A: Physicochemical and Engineering Aspects, 151: 389-397). Solid sulphur is thus found in the bioreactor effluent and is available for use in agriculture along with the other nutrients (N, P, and K). This fertilizer can significantly enhance agricultural yields, particularly for vegetable crops (Grant et al., 2007, Canadian Journal of Plant Science, 87: 293-296).

In an AD bioreactor, sulphate-reducing bacteria (SRB) and hydrogenotrophic methanogens (HM) compete for the hydrogen available in the liquid phase. Dissolved hydrogen results from the hydrolysis and acidogenesis associated with the microbial activities. The SRB use this $H_2$ to form $H_2S$, which, in high concentrations, has an inhibitory effect on the HM as well as on the SRB. The specific methane yield can therefore be affected by high sulphur contents in the substrate being treated.

Jenicek et al. (2008, Water Science & technology, 58: 1491-1496) studied the impact of air dosing on two mesophilic AD bioreactors (BR1 and BR2) treating activated sludges. Air was injected into the sludge recirculation loop. The applied $O_2/S^{2-}$ ratio was between 3.7 for BR1 and 5.5 for BR2. The $H_2S$ concentration without air injection was 3084 ppm for BR1 and 5338 ppm for BR2. The results indicated an average $H_2S$ reduction of 99% over several years of operation, with concentrations in the effluent of between 29 ppm and 50 ppm. It was also observed that microaerobic conditions did not reduce process performance. The specific $CH_4$ yield for BR2 increased 50% following air injection and remained unchanged in the other bioreactor. For BR2, the ratio of volatile solids to total solids in the effluent was 65.8 in a strictly anaerobic environment and 59.7 in a microaerobic environment, and remained unchanged in BR1. To explain the improvement in the performance of BR2, it is hypothesized that the bioreactor was inhibited by high $HS^-$ concentrations before oxygenation started. This method relies on the control of the oxygen injection in function of the amount of sulphur present in the influent (ratio $O/S^{-2}$). Sulphur analysis is an expensive and fairly complex analysis, which is not suited for agricultural application.

Khanal et al. (2003, Journal of environmental engineering, ASCE, 129: 1104-1111) used oxidation-reduction potential (ORP) as a controlling parameter to regulate $O_2$ dosing in an upflow mesophilic AD biofilter system. Such filters are commonly employed in the treatment of waste water. Variable sulphate loads were applied (1000, 3000 and 6000 mg $L^{-1}$) for a constant organic loading rate (18 g of chemical oxygen demand per liter). The reactor was initially operated under anaerobic conditions at a natural ORP (between −290 and −300 mV) and the ORP level was then increased by +25 mV through oxygenation of the liquid phase. It was demonstrated that $O_2$ dosing reduced the sulphate concentration in the effluent by more than 98%. It was noted that the sulphur was primarily converted to the $S^0$ form. It was also observed that part of the $O_2$ was used for facultative aerobic processes and that this helped protect the methanogens from inhibition by the $O_2$, particularly for lower sulphate loads. Hence, again under microaerobic conditions, methane production rates of 15.5% and 6.2% lower than the natural ORP level were observed for sulphate loads of 1,000 and 3,000 mg $L^{-1}$, respectively. This study has been carried out with municipal wastes, which are not representative of agricultural wastes. For example, animal manures contain higher concentration of nitrogen that normally affects mesophilic anaerobic digestion processes when it exceeds 3000 to 4000 mg/L.

Van der Zee et al. (2007, Bioressource Technology, 98: 518-524) applied microaerobic conditions to an anaerobic fluidized bed bioreactor fed with vinasse at a sulphur loading rate of 1.3 mmol S $d^{-1}$. Introduction of an air flow corresponding to an $O_2$/S molar ratio of 8-10 (1.5 L $d^{-1}$) was sufficient to reduce the $H_2S$ concentration in the effluent to undetectable levels (<0.02%). The oxidation reaction of the $H_2S$ appears to compete with aerobic organic matter breakdown processes. This article also described experiments under microaerobic conditions conducted in batch mode, the results of which demonstrated that the sulphur was oxidized primarily to the elemental form. The approach proposed in this study requires laboratory analysis of the substrate to quantify the sulfur concentration in the substrate. Also the substrate used is not representative of livestock manure.

There is still a need to be provided with method of removing hydrogen sulphide from biogas resulting from agriculture waste.

It would be thus highly desirable to be provided with a process that eliminates hydrogen sulphide from biogas resulting from agriculture waste that is low in cost, is very stable, simple, easy to operate and which does not interfere with regular farm operations.

SUMMARY

In accordance with the present description there is now provided a process for reducing hydrogen sulphide concentration in a biogas comprising the steps of supplying air in a psychrophilic anaerobic bioreactor producing biogas, the bioreactor comprising a gas phase and a liquid phase containing an anaerobic sludge, and removing hydrogen sulphide from biogas by oxidation to elemental sulphur.

It is also provided a process for reducing hydrogen sulphide concentration in a biogas comprising the steps of supplying air in a psychrophilic anaerobic bioreactor producing biogas, the bioreactor comprising a gas phase, and a liquid phase containing an anaerobic sludge, and removing the converted sulphur from the hydrogen sulphide from the bioreactor.

In an embodiment, additional biogas is supplied from at least one adjacent bioreactor connected to the psychrophilic bioreactor.

In another embodiment, the process described herein further comprises the step of feeding the psychrophilic bioreactor with an organic substrate.

In another embodiment, the organic substrate is a liquid substrate, a semi-liquid substrate or a solid substrate such as for example, but not limited to, a live-stock waste, an agricultural waste, a municipal waste, an agri-food waste, an industrial organic waste, or a mixture thereof. The live-stock waste can be an animal waste, such as but not limited to, a cattle manure, a pig manure, a poultry manure, or a mixture thereof.

In an additional embodiment, the psychrophilic bioreactor is at a temperature between 5° C. to 30° C.

In another embodiment, the biogas is mixed with air.

In a further embodiment, the biogas-air mixture is bubbled into the liquid phase of the psychrophilic bioreactor.

In an additional embodiment, the flow rate of injected air is between 2 to 20% of the flow rate of biogas.

It is also provided herein a process for reducing hydrogen sulphide concentration in a biogas comprising the steps of supplying a first psychrophilic bioreactor with air and biogas, the biogas provided from a second bioreactor, the first psychrophilic bioreactor comprising a sludge; and removing hydrogen sulphide from biogas by oxidation to elemental sulphur.

It is also additionally provided a process for reducing hydrogen sulphide concentration in a biogas comprising the steps of supplying a first psychrophilic bioreactor with air and biogas, the biogas provided from a second bioreactor, the first psychrophilic bioreactor comprising a sludge; and removing the converted sulphur from the hydrogen sulphide from the first bioreactor.

In an embodiment, the first psychrophilic bioreactor comprises a gas phase. The first psychrophilic bioreactor can further comprise a liquid phase.

In another embodiment, the sludge is contained in the liquid or gas phase of the first bioreactor.

The process described herein can also comprise the step of inoculating the first psychrophilic bioreactor with a sludge collected from a second psychrophilic bioreactor.

In another embodiment, the sludge has been acclimated to a solid or a liquid organic substrate.

BRIEF DESCRIPTION OF THE DRAWINGS

Reference will now be made to the accompanying drawings.

DETAILED DESCRIPTION

It is provided a non-polluting, easy-to-operate, efficient and cost-effective biological process for removing hydrogen sulphide from biogas. The process involves injecting a small quantity of air into the gas phase or the liquid phase of a psychrophilic bioreactor to allow microbial flora to convert the hydrogen sulphide into elemental sulphur, which does not affect the lifespan of biogas-fueled equipment.

The present description deals with the evaluation of the performance of a biological process designed to reduce the concentration of hydrogen sulphide ($H_2S$) present in biogas. Air is supplied to the liquid or gas phases of a bioreactor that contains anaerobic sludge in order to provide microaerobic condition to the anaerobic facultative microflora. This disclosure is specifically focused on anaerobic psychrophilic sludges (530° C.) acclimated to several organic substrates such as agricultural, agrifood, municipal or industrial waste as well as energy crops.

The aim of a first experiment described herein was to evaluate the biotransformation potential of sludges not fed with liquid manure and subjected to a known $H_2S$ load (between 1.0 and 3.3 mg $H_2S$ $L^{-1}$ sludge $h^{-1}$) injected into the liquid phase at the base of the bioreactor. A maximum biotransformation rate of 1.27 mg $H_2S$ $L^{-1}$ sludge $h^{-1}$ was obtained, a capacity 6.7 times higher than the maximum $H_2S$ production rate obtained for a bioreactor fed with liquid cattle manure (0.19 mg $H_2S$ $L^{-1}$ sludge $h^{-1}$). A second experiment involved evaluating the impact of this process on the methane yield and stability of an operating bioreactor. Two psychrophilic bioreactors were operated in semi-batch mode and fed in an identical manner with liquid cattle manure. Only one of the two bioreactors was operated under microaerobic conditions. This bioreactor had undetectable $H_2S$ concentrations except on the days when the air/biogas volume ratio was less than 0.056. Concentrations ranging from 0 to 3500 ppm were measured in the gas effluent of the bioreactor without air injection. The bioreactor operated under microaerobic conditions had a specific methane yield 6.5% lower than the control bioreactor, but this difference dropped to 0.87% for the last four cycles of the experiment. This can be explained by the reduction of the air flow rate during that period; down to 4 mL/min.

Another experiment involved evaluating the potential of psychrophilic AD sludges to biotransform $H_2S$ into $S^0$ when subjected to microaerobic conditions. The sludges were not fed with liquid manure in order to eliminate the contribution of this substrate to the gas volume balance as well as to the sulphur mass balance. The residual biogas production of these unfed sludges was measured separately in another tank, which served as a control.

Figure 1:
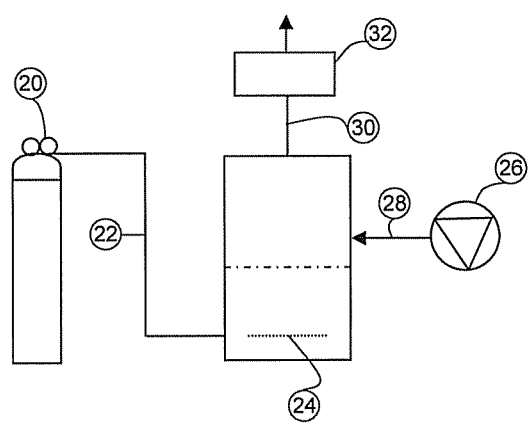
FIG. 1 illustrates an experimental setup, consisting of a laboratory bioreactor.

FIG. 1 illustrates the experimental setup, consisting of a laboratory bioreactor. Each of the reference numerals refer to the following:

20. synthetic biogas;
22. mass flow meter;
24. diffuser;
26. air injection pump;
28. mass flow meter;
30. gas sampling;
32. volumetric gas meter.

A 40 L bioreactor was located in a temperature-controlled room (25° C.) and inoculated with 15 L of sludges from a psychrophilic AD bioreactor. These sludges, which came from the Agriculture and Agri-Food Canada laboratories (Lennoxyille, Quebec), were acclimated to liquid pig manure and were operated in batch mode (Masse et al., 2000, Canadian Agricultural Engineering, 42: 131-137).

A standardized artificial biogas (Air liquid mixture—70.9% $CH_4$—28.7% $CO_2$—0.385% $H_2S$) was bubbled in at the base of the bioreactor using an aquarium diffuser made from a perforated rubber tube (Elite, L=89 cm, dia.=0.5 cm). A standard volume flow rate of this biogas (between 0 and 100 mL/min) was assured by a mass flow meter/controller (Dwyer GFC17, accuracy 1.5%), specifically calibrated by the supplier to receive this gas mixture.

Air was injected into the gas phase using a peristaltic pump coupled to a pressure regulator. A second mass flow meter/controller (FMA-2617, accuracy 0.2%) was used to adjust the standard volume flow rate of air between 0 and 50 mL/min.

The gas phase was analyzed three to five times a week by a Carle 400 AGC gas chromatograph (GC) ($CH_4$, $CO_2$, $N_2$ and $H_2S$). Colorimetric tubes were used to measure lower $H_2S$ concentrations (Kitagawa, Model 8014-120SM, range: 50-2000 ppm). The $O_2$ concentration was measured with a Critical Environment electrochemical sensor (MAC-EOO2, range: 0-25%, accuracy: 0.4%). The total sulphur concentration of the liquid phase was measured at the beginning and at the end of the experiment using a LECO analyzer (Model SC444DR, Laboratoires d'analyses SM Inc., Varennes, QC, Canada). This involved extracting the liquid phase from the bioreactor which was then mixed and sampled. The solids at the surface of the liquid and adhering to the walls of the gas phase of the bioreactor were recovered at the end of the experiment and also analyzed for total sulphur. Total solids (TS) and pH were measured according to a known standard method (APHA 1992).

Figure 3:
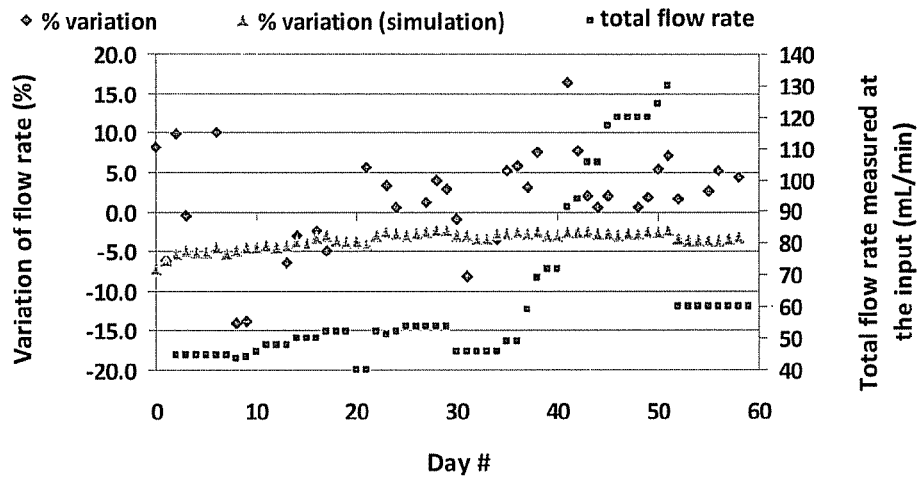
FIG. 3 illustrates the measured rate of decrease of the flow-rate (input-output) in the batch reactor.

FIG. 3 presents the rate of decrease of the total volume flow rate between the input and output of the bioreactor throughout the experiment. The results show a drop in the volume flow rate of between 0% and 15% for the last 25 days of operation, with an average reduction of 4.6%. Because of the variability observed with this parameter, any solid conclusions could not be drawn and it was difficult to correlate these observations with the operating conditions. There were also doubts about the validity of the output measurement and questions were raised about the accuracy of the measuring instrument itself. It was therefore decided to use the flow rates measured at the input (thermal mass flow rate) to estimate the volume at the output.

Figure 4:
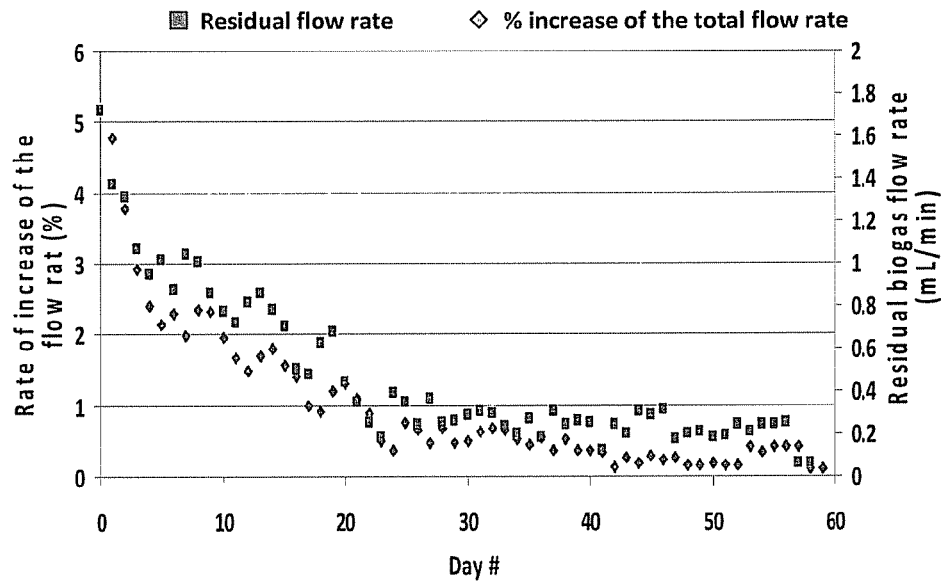
FIG. 4 illustrates the measured decrease of residual biogas production in the reactor.

This volume flow rate was used to estimate the $H_2S$ conversion rate discussed hereinbelow. FIG. 3 also presents the simulation of the rate of volume decrease, which is based on the estimate of the flow rate at the output. For this simulation, it was first considered that humidification of the biogas increased the volume of biogas injected by 3.3%, assuming that the biogas will be saturated following the bubbling in the liquid phase. In addition, a reduction in volume was included in order to take into account the conversion of $H_2S$ and the consumption of $O_2$, which represents a decrease of up to 0.4% and 0.2%, respectively, relative to the input volume. FIG. 4 presents the residual daily biogas production of the sludges used for this experiment, which was also incorporated in the simulation. This biogas production was measured in a separate tank.

Figure 5:
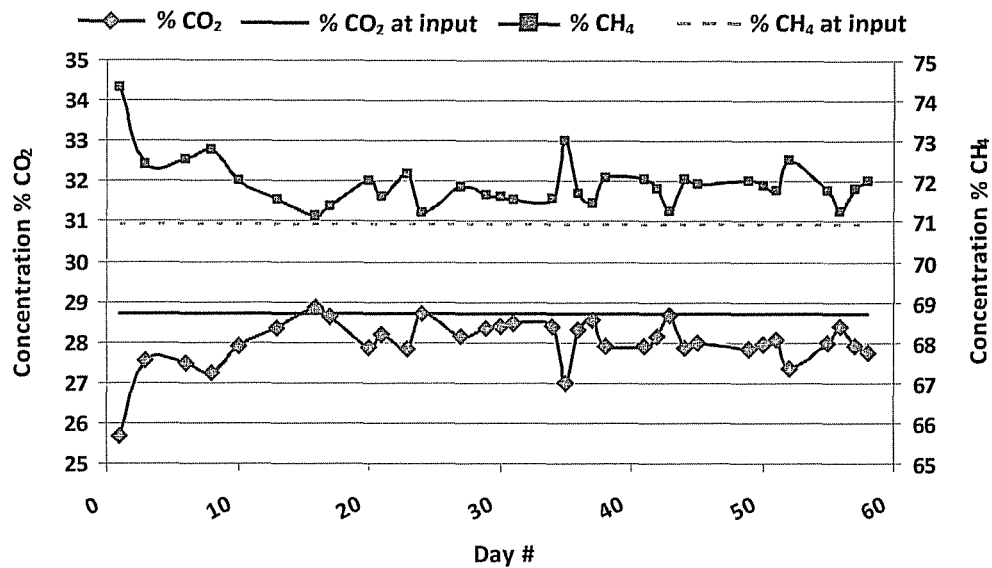
FIG. 5 illustrates the concentration in $CO_2$ and $CH_4$ in the gas effluent composition.

In total, 35 daily gas effluent samples were analyzed by GC during the 60 days of the experiment. FIG. 5 presents the results of these analyses for $CH_4$ and $CO_2$, which yield an average $CH_4/CO_2$ ratio of 2.56±0.01, compared to 2.47±0.01 (four samples) for the standard mixture injected into the bioreactor. This higher $CH_4$ concentration can be explained by the action of hydrogenotrophic methanogens, which use $CO_2$ and hydrogen to form methane. This hydrogen appears to come from the residual hydrolysis of the solids present in the sludges. For the first 15 days of the experiment, the average $CH_4/CO_2$ ratio was 2.66±0.01. This slightly higher ratio also coincided with the period of greatest hydrolytic activity of the sludges (see FIG. 4). In any event, this phenomenon had no impact on the volume balance.

Figure 6:
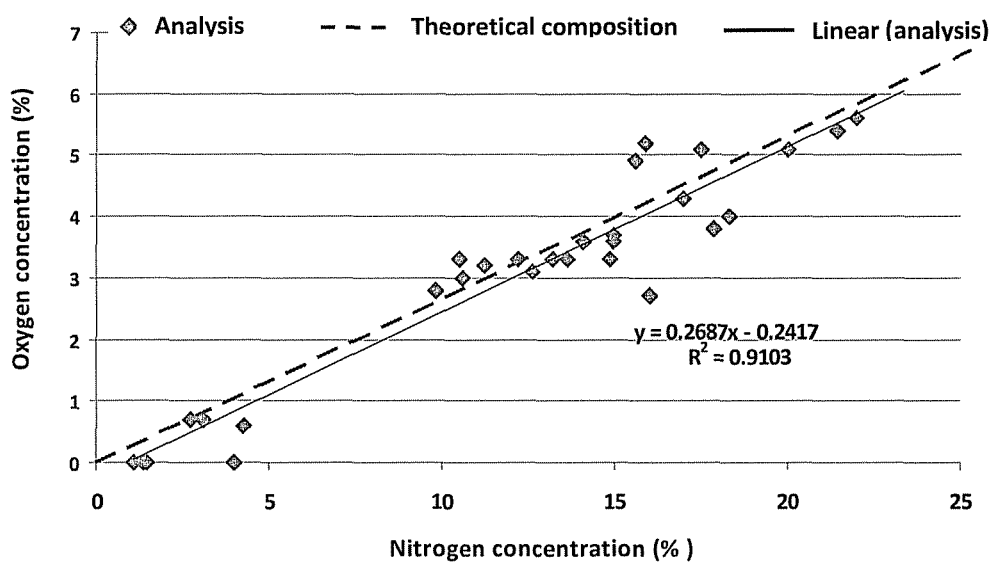
FIG. 6 illustrates the concentration of oxygen in the gas effluent composition.

FIG. 6 can be used to compare the theoretical $O_2/N_2$ ratio of the air with the gas phase analysis results. The slope of the trend curve shows an $O_2/N_2$ ratio that is 1.1% lower than that of the air (0.266), a difference that is considered negligible. However, the disparity of the values can be attributed to the inadequate accuracy of the measuring devices, which makes it impossible to accurately estimate the quantity of oxygen consumed. In fact, the nitrogen concentrations measured (average of 13.2%) are higher than the standard used (1% $N_2$) to calibrate the GC. However, stoichiometrically, 0.5 mL of $O_2$ is required for each mL of $H_2S$ broken down. This corresponds to 0.1% of the total volume injected at the input for the highest conversion rate obtained during this experiment. Hence, oxygen consumption is considered negligible in the gas volume balance.

Figure 7:
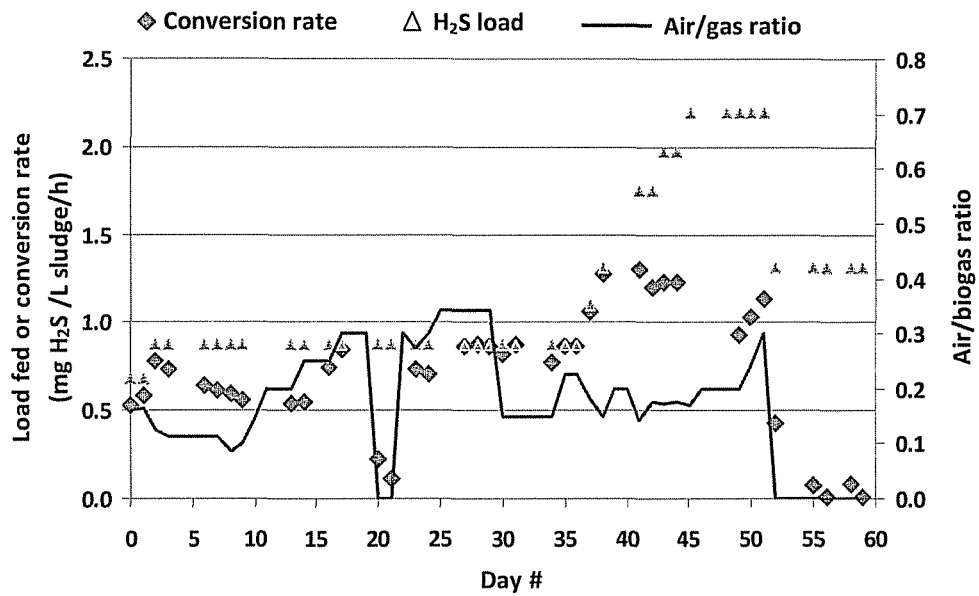
FIG. 7 illustrates a graphic representation of the $H_2S$ conversation rate.

FIG. 7 presents the $H_2S$ conversion rate as a function of the load applied as well as the air/biogas ratio. The maximum conversion rate was obtained on day 38, with 0.318 mg $H_2S$ $min^{-1}$, equivalent to 1.27 mg $H_2S$ $L^{-1}$ sludge $h^{-1}$. This represents 97.2% conversion of the load applied (1.31 mg $H_2S$ $L^{-1}$ $h^{-1}$). This conversion rate is 6.7 times higher than the rate observed for a bioreactor fed with liquid cattle manure, i.e. 0.19 mg $H_2S$ $L^{-1}$ sludge $h^{-1}$. By the third day of operation, 4.1 times this conversion rate was obtained, with 0.78 mg $H_2S$ $L^{-1}$ sludge $h^{-1}$ (91% conversion). This high yield is obtained because the oxygen is not used for facultative aerobic processes as in the case of an operating bioreactor, since little organic matter is available. Hence, the oxygen would be particularly available to oxidize the $H_2S$. Moreover, it was confirmed on days 20 and 21 that the process is aerobic, since an accidental shutdown of the air injection pump caused a drop in the conversion rate to 0.028 mg $H_2S$ $min^{-1}$.

Figure 8:
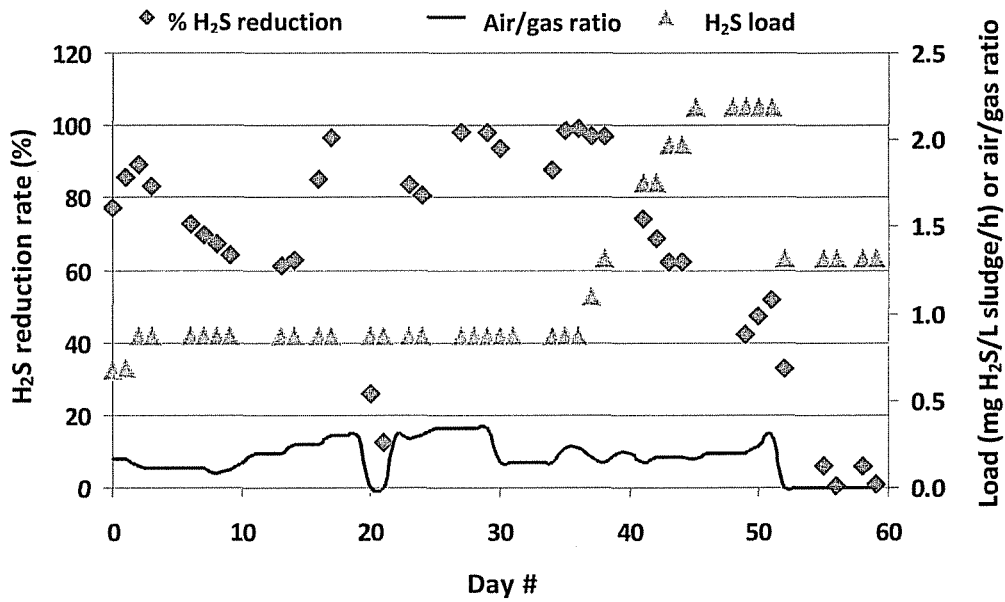
FIG. 8 illustrates a graphic representation of the $H_2S$ reduction rate.

Starting on day 36, the load was gradually increased, while maintaining an air/biogas ratio of between 0.15 and 0.20. The conversion rate leveled off on day 38 despite the continuously increasing $H_2S$ load. Between day 43 and day 49, the conversion rate fell 25% despite the conditions being maintained. FIG. 8 shows the rate of reduction of $H_2S$ in the effluent as a function of the load. It can be seen that beginning on day 41, efficiency drops off quickly to unacceptable levels. In fact, between day 41 and day 50, the $H_2S$ concentration in the effluent rose from 400 to 1300 ppm.

From the beginning of the experiment, a solid deposit formed on the surface of the liquid, especially on the walls of the bioreactor where the greatest accumulation appeared at a height of approximately 2 cm above the liquid. In addition, a yellowish powder was present on all the walls of the gas phase. In total, 32 g of a greyish deposit was recovered, which contained a high concentration of solids (39% TS). The total sulphur analysis showed that this deposit contained 1.59 g of sulphur, or 15.6% of the sulphur accumulated in the bioreactor over the course of the experiment (12.40 g S).

Table 1 presents the balance of the solids recovered in the liquid phase, excluding the above-mentioned solid deposit recovered at the surface. These results are based on two samples, taken at the beginning and end of the experiment. It was observed that the sulphur concentration of the solids increased, but the balance between the beginning and the end was nevertheless negative. This was contrary to expectations. The decrease in solids content can be explained by continuation of the hydrolysis process, but this does not explain the negative sulphur balance. The most plausible hypothesis is that the sampling method caused a loss of solids.

TABLE 1

Balance of the solids recovered

| | Initial | Final | Balance |
| --- | --- | --- | --- |
| Mass of the liquid phase (kg) | 15.000 ± 0.001 | 14.960 ± 0.001 | −0.1 |
| Total solids (%) | 4.28 ± 0.03 | 3.59 ± 0.05 | N/A |
| Total solids (g) | 642 | 535 | −105 |
| Total sulphur (%) | 1.05 ± 0.01 | 1.19 ± 0.01 | N/A |
| Total sulphur (g) | 6.74 | 6.37 | −0.35 |

However, the accumulation of sulphates in the liquid phase is unlikely, since this would have caused a drop in pH in the liquid phase. On the contrary, this parameter increased from 7.81 at the beginning of the experiment to 7.92 at the end of the experiment. This is consistent with the hypothesis that limited oxygen conditions promote the formation of $S^0$ rather than sulphates.

Figure 2:
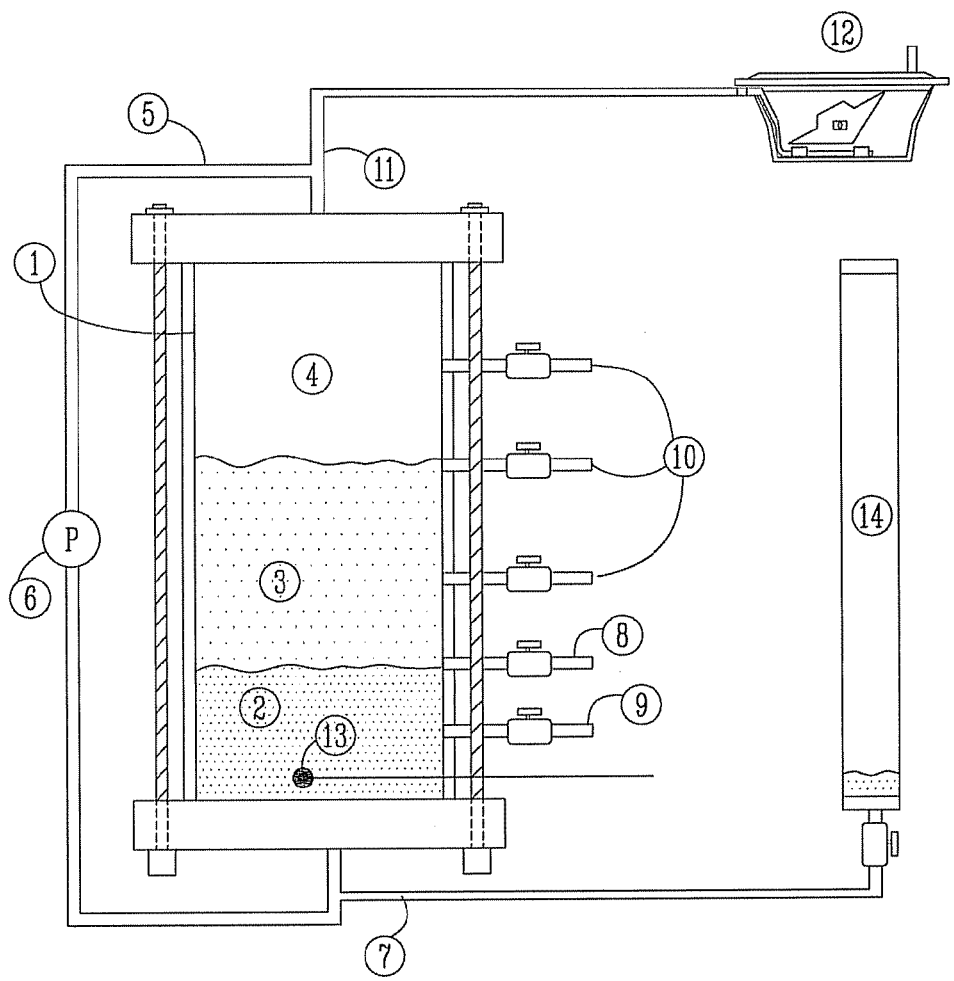
FIG. 2 illustrates a schematic representation of a sequencing batch reactor.

Another experiment involved evaluating the potential of psychrophilic AD sludges to biotransform $H_2S$ in a sequencing batch reactor. FIG. 2 illustrates the experimental setup, consisting of a laboratory scale sequencing batch reactor (SBR) as described in Canadian patent No. 2,138,091, the content of which is enclosed herewith by reference. Each of the reference numerals refer to the following:

1. bioreactor;
2. sludge bed zone;
3. treated effluent;
4. gas space;
5. biogas recirculation line;
6. biogas pump;
7. feeding line;
8. treated effluent removal port;
9. sludge sampling port;
10. mixed liquor or supernatant sampling port;
11. gas outlet;
12. biogas flow meter;
13. thermocouple; and
14. feeding system.

Figure 9:
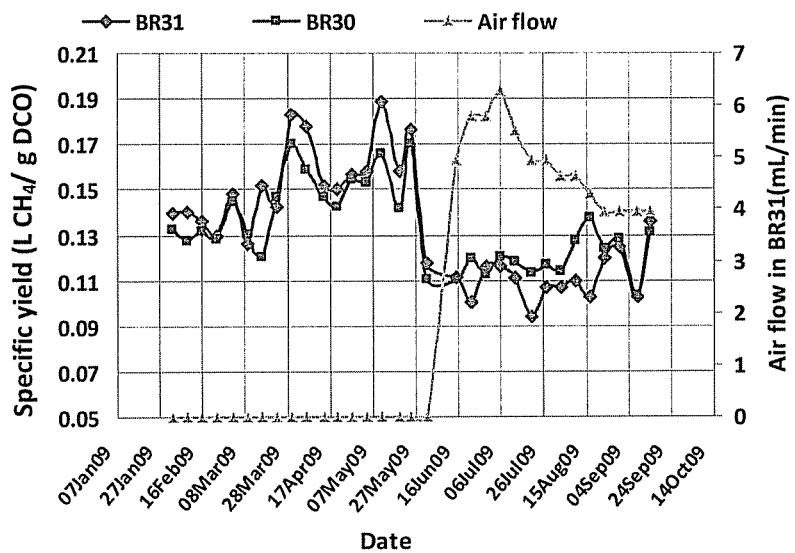
FIG. 9 illustrates methane yield in a control bioreactor (BR30) and in a bioreactor under microaerobic conditions (BR31).

FIG. 9 presents the specific $CH_4$ yield curve for the two bioreactors before and after the start of air injection (see Jun. 15, 2009). For the digestion cycle prior to this date, the loading rate was increased by 33% for reasons independent of this experiment. In addition, beginning on Jun. 15, 2009, there was a change in the level of the liquid manure mixture fed to the bioreactors. A 20% drop in specific $CH_4$ yields was observed for the two bioreactors following changes in operating conditions.

For the air injection period (10 digestion cycles=70 days), the average yield was 0.120 L $CH_4$ $g^{-1}$ COD for the control bioreactor (BR30) and 0.112 L $CH_4$ $g^{-1}$ COD for the bioreactor under microaerobic conditions (BR31). The yield of BR31 was therefore 6.7% lower than BR30. The injection of air thus reduced the specific $CH_4$ yield. However, for the last four cycles, the difference between the bioreactor yields narrowed, with the result that, for this period, the yield of BR30 was 0.87% higher than BR31. This difference is too low to be considered significant. In fact, before Jun. 15, 2009, the yield of BR30 was on average 2.9% lower than BR31. The average reduction in the difference for the last four cycles of the experiment could be explained by the decrease in the air flow rate (see FIG. 8).

Table 2 presents the main performance parameters of the bioreactors during the air injection period. There were no significant differences in the bioreactors in terms of the rate of reduction of TS, volatile solids (VS) and total chemical oxidation demands (TCOD). The same is true for volatile fatty acids measured in the effluent. Table 2 presents the results for acetic acid and proprionic acid only. An accumulation of these acids would normally have been caused by an imbalance in the bacterial flora.

TABLE 2

Parameters of the bioreactors

| Operating parameters | BR30 | BR31 |
|---|---|---|
| % reduction in TS | 35 ± 8 | 33 ± 8 |
| % reduction in VS | 40 ± 9 | 39 ± 9 |
| % reduction in TCOD | 39 ± 10 | 37 ± 11 |
| Acetic acid in effluent (mg/L) | 58 ± 13 | 62 ± 19 |
| Proprionic acid in effluent (mg/L) | 4 ± 2 | 4 ± 2 |

Figure 10:
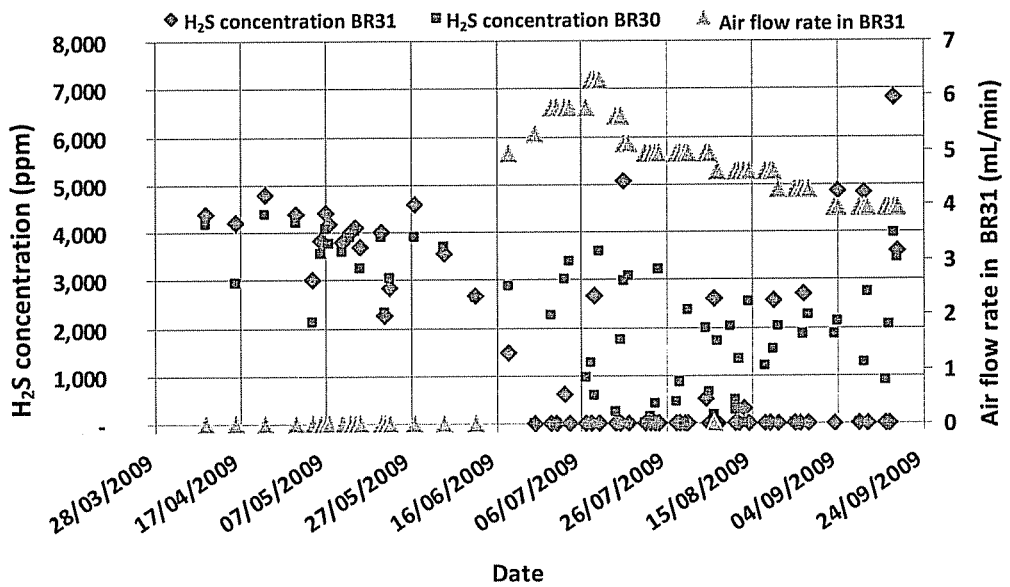
FIG. 10 illustrates the $H_2S$ concentration in the gas effluent in the bioreactor BR30 and BR31.

FIG. 10 presents the GC analyses of the $H_2S$ concentration throughout the experiment. The concentrations have been corrected so that they can be expressed without nitrogen, in order to make the results comparable. In fact, the AD process does not produce nitrogen and, in addition, the quantities found in the gas effluent vary over the course of a cycle, affecting the $H_2S$ concentration measured.

A generalized decline in the $H_2S$ concentration was observed after Jun. 15, 2009, possibly attributable to the change in liquid manure on this date. The average $H_2S$ concentration for BR30 thus declined from ±3527 ppm for the period prior to air injection presented on this graph to ±1435 ppm after. Nevertheless, a marked difference was observed between the two bioreactors, after the start of air injection. More specifically, BR30 had undetectable concentrations (<300 ppm) up to 3958 ppm $H_2S$; 20% of these 50 analyses had undetectable concentrations compared with 75% of analyses in the case of BR31. The colorimetric tube analyses confirmed undetectable concentrations (<50 ppm) for BR31 21 times, compared to only once for BR30.

Figure 11:
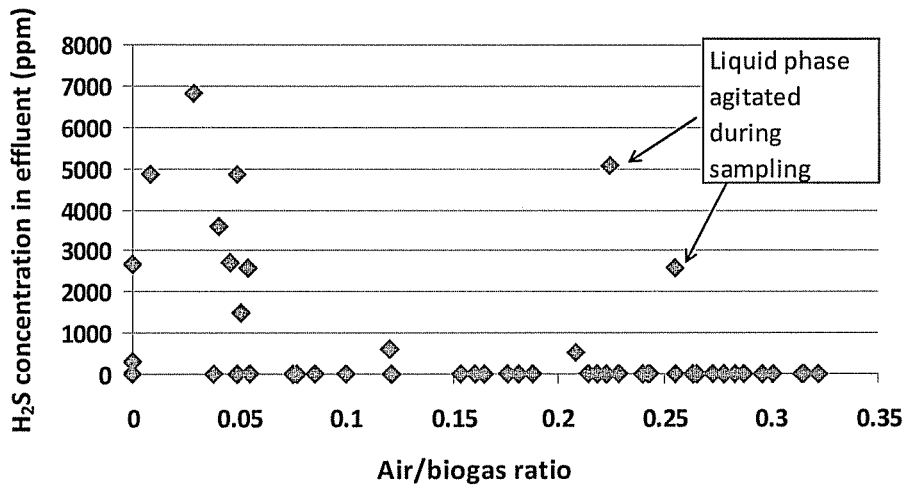
FIG. 11 illustrates the $H_2S$ concentration as a function of air dosing.

In addition, eight of the 10 analyses for which $H_2S$ was detected in BR31 occurred on the same day of the cycle, i.e. the fourth day. This was the day on which biogas production was highest (21 to 35 L $CH_4$ $d^{-1}$). It can therefore be hypothesized that air dosing was inadequate for these days, considering that the pump is not controlled in real time as a function of the biogas production level. FIG. 11 supports this hypothesis since $H_2S$ was detected only for low nitrogen concentrations (<4.3%). The two values identified on the graph represent days on which the liquid phase was agitated in error shortly before the sample was taken. This agitation caused a one-time release of the $H_2S$ dissolved in the liquid phase.

Figure 12:
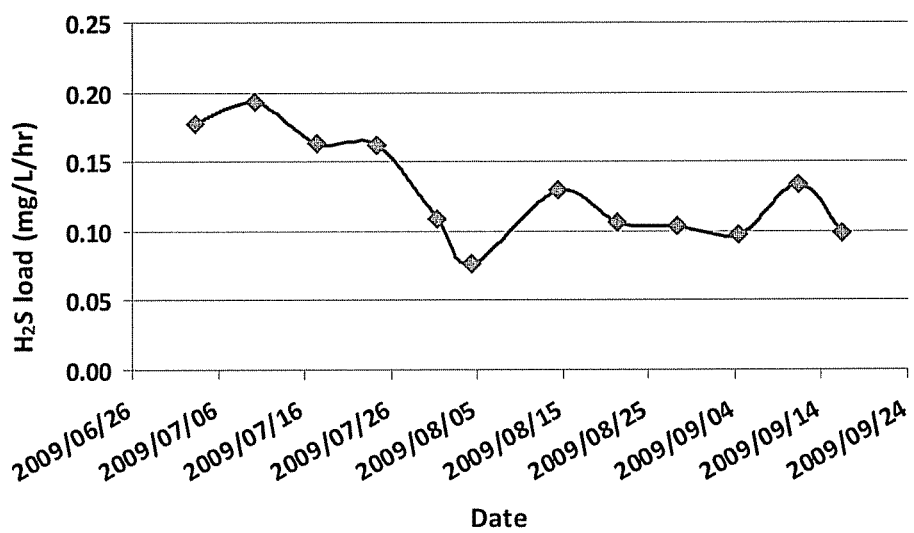
FIG. 12 illustrates the maximum $H_2S$ load per cycle in the BR30 reactor.

FIG. 12 presents the maximum $H_2S$ load for each cycle during the air injection period, but for BR30 only (anaerobic). Loads up to 0.064 mg*$min^{-1}$ were observed, equivalent to 0.19 mg $H_2S$ $L^{-1}$ $h^{-1}$. There was no detectable $H_2S$ in the gas effluent of BR31 for this day (<50 ppm or 0.0025%) and the air/biogas ratio was 0.19.

It is demonstrated herein that injecting air into the gas phase of an AD bioreactor operating at low temperature and feed with liquid cattle manure reduces the biogas $H_2S$ concentration to levels below 50 ppm. It appears to be preferable to control air dosing as a function of biogas production, in order to maintain a minimum air concentration of between 5% and 6%. This is particularly true for batch operation. Biogas dilution is thereby minimized, while maintaining system performance at the same level as under perfectly anaerobic conditions. The presence of oxygen in the gas phase did not significantly affect specific methane yields, with less than 1% difference with the control reactor for the last four digestion cycles. System stability was not compromised by the microaerobic conditions.

However, the psychrophilic AD sludges not fed with a substrate offer a higher $H_2S$ conversion capacity compared to a bioreactor fed with liquid manure. Bubbling of an artificial biogas into sludges was effective in removing up to 1.27 mg $H_2S$ $h^{-1}$ $L^{-1}$ from the effluent, for a conversion rate of 97.2%. This is a conversion capacity 6.7 times higher than the maximum $H_2S$ production rate observed in a bioreactor fed with liquid cattle manure (0.19 mg $H_2S$ $h^{-1}$ $L^{-1}$). A portion of the sulphur (15.6%) was recovered at the surface of the liquid as well as on the walls of the gas phase bioreactor.

In order to validate the experimental montage described hereinabove on an actual on-farm context, a pilot unit was installed in February 2011 on the Péloquin farm in the village of St-Edwidge de Clifton, Canada. Results obtained on this site showed performances exceeding those observed in laboratory. Optimization assays were conducted on two different configurations of a bubble column inoculated (100, 110) with on-farm methanisation sludge, and pumped from the manure digester system in operation at the Péloquin farm (see FIGS. 13 and 14).

Figure 13:
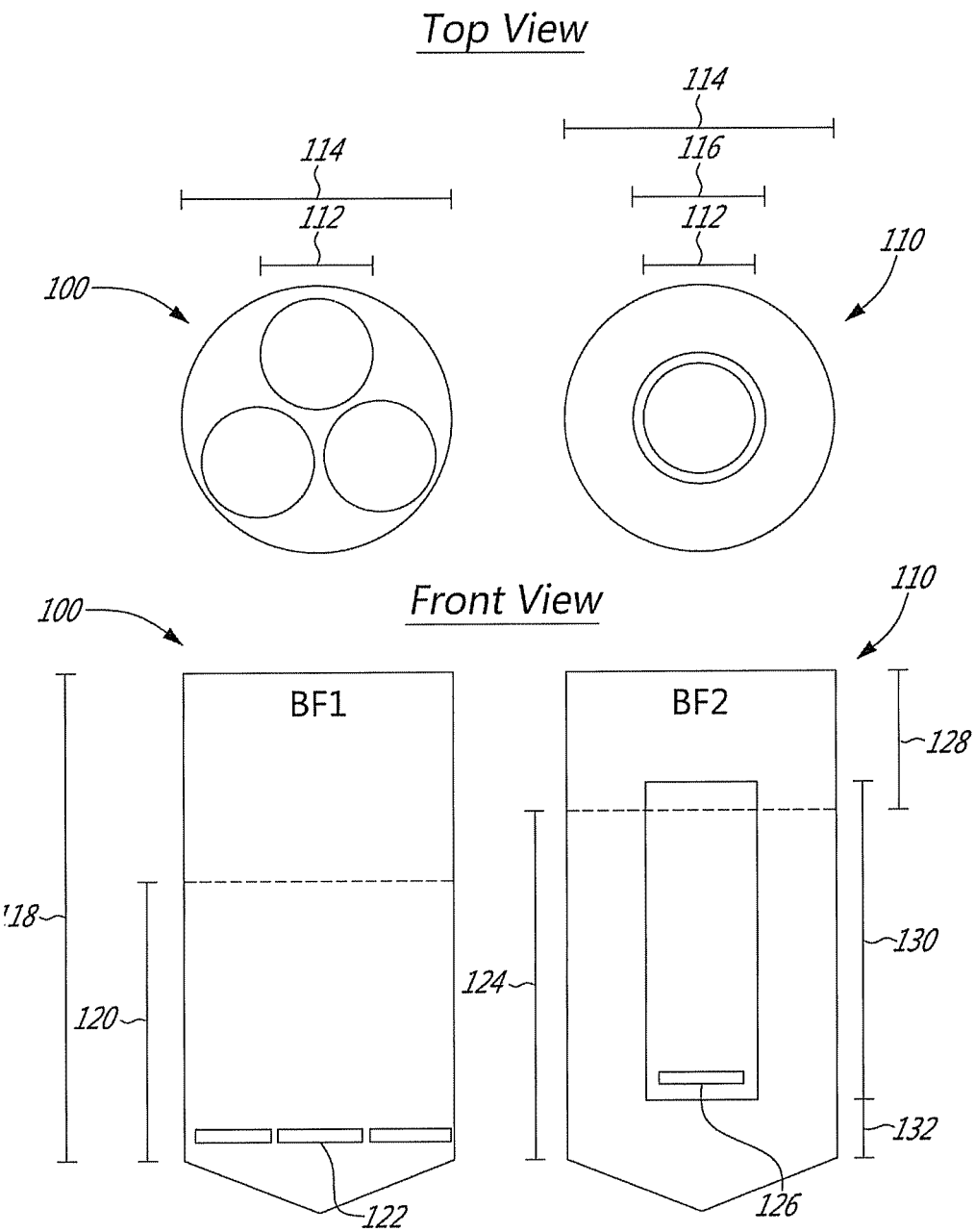
FIG. 13 illustrates bubble column configurations used in a pilot bioreactor unit in on a farm.
Figure 14:
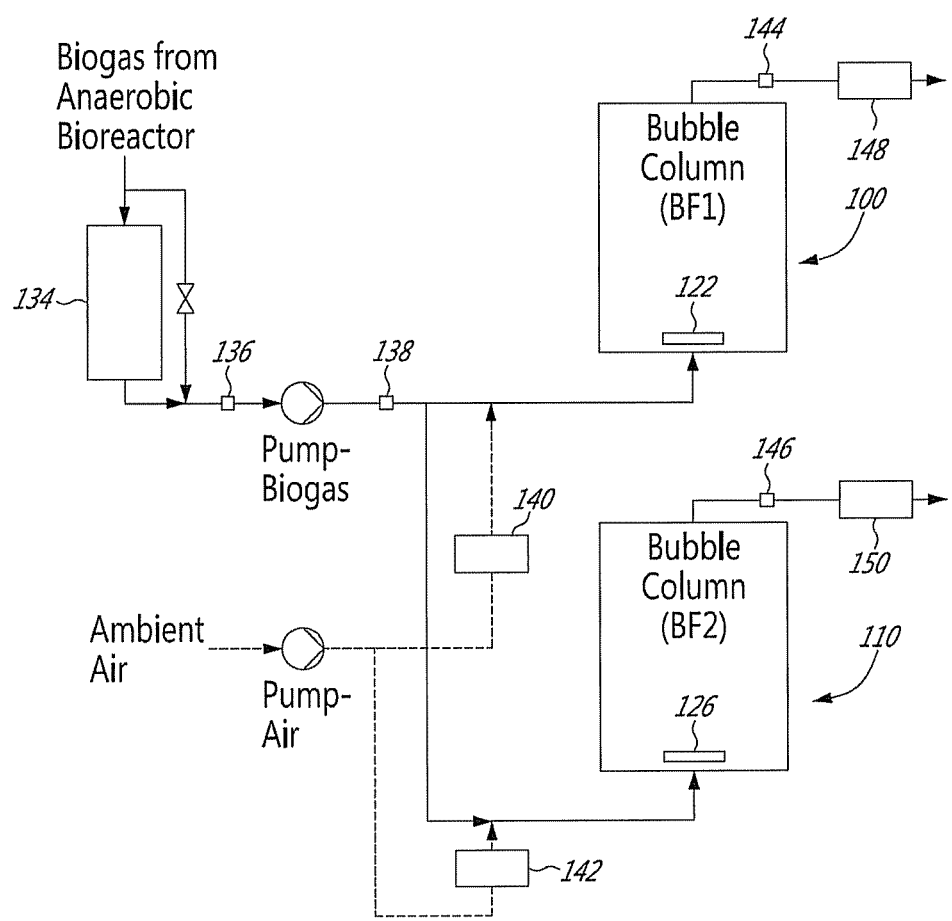
FIG. 14 illustrates the process flow diagram of the pilot unit experiment.

FIG. 13 illustrates the bubble columns 100, 110 setup. Each of the reference numerals refer to the following:
  100. Bubble column BF1
  110. Bubble column BF2
  112. Diameter of an EPDM diffuser (25.4 cm)
  114. Diameter of a bubble column (BF1 and BF2) (60.96 cm)
  116. Diameter of a diffusion column (30.48 cm)
  118. Height of bubble columns (BF1 and BF2) (152.4 cm)
  120. Height of sludge in BF1 (86.36 cm)
  122. Set-up of the 3 diffusers in BF1
  124. Height of sludge in BF2 (121.92 cm)
  126. EDPM diffuser installed in BF2
  128. Headspace of BF2 (30.48 cm)
  130. Height of the diffusion column in BF2 (114 cm)
  132. Clearance between the base of BF2 and the diffusion column (15.24 cm)
  160. Drain valve
  162. Drain valve FIG. 14 illustrates the process flow diagram of the pilot unit configuration. Each of the reference numerals refer to the following:
  134. Chemical pretreatment
  136. Sampling port #1 (inlet biogas if $H_2S$<2000 ppm)
  138. Rotameter
  140. Thermal mass flow controller (air)-BF1
  142. Thermal mass flow controller (air)-BF2
  144. Sampling port #3 (outlet of BF1)
  146. Sampling port #4 (outlet of BF2)

148. Mass flow meter-BF1
150. Mass flow meter-BF2

Air was added to the biogas (ratio 5:100) and the mix was bubbled in the liquid sludge (approx. 3% solids). No product was added to the sludge. Oxygen concentration in the biogas was about 1%. Microaerobic condition promotes the biochemical reaction of hydrogen sulphur ($H_2S$) being transformed into elemental sulphur ($S^0$), with oxygen as the electron acceptor. The facultative aerobic microorganism involved (genus *Thiobacillus*) are naturally present in anaerobic sludge. The sulphur saturated sludge was purged into the methanisation system effluent tanks, after several weeks of operations. The solid elemental sulphur of biologic origin will contribute to the fertilizing potential of this effluent, a high-quality fertilizer.

Bubble column #2 110 presented the best performances in term of conversion rate of $H_2S$ and % of $H_2S$ concentration reduction. The best conversion rate measured was 2.4 mg $H_2S/L/h$, for a % of reduction of 94%. In addition, the performance of this column 110 was even better when a higher concentration of $H_2S$ was tested at the inlet of the bubble column 136. The column #1 100 presented lower performances (>2000 ppm at outlet) for high concentration at the inlet 136 (4000-5000 ppm). The methane concentration was not significantly affected by the transition in a bubble column. The measurements were consistent with what was expected from the dilution of the biogas by air. The oxygen concentration decreased at the exit when the column reached the most important conversion rate performance. A concentration of 0.8% was measured when the column #2 110 reached is highest conversion rate of $H_2S$. The oxygen consumption calculated with stoichiometric equation was consistent with the amount of sulphur assumed to be bio-transformed. The inoculum was used over a period of 48 days without showing any decrease in performance.

Thus, present disclosure clearly provide the demonstration of that the non-polluting, easy-to-operate, efficient and cost-effective biological process for removing hydrogen sulphide from biogas described herein was applicable at an on-farm bioreactor unit.

The present disclosure will be more readily understood by referring to the following examples which are given to illustrate embodiments rather than to limit its scope.

Example I

AD Bioreactors Fed with Liquid Cattle Manure

The experiment involved confirming that injecting air into the gas phase of an AD bioreactor fed with liquid cattle manure reduces the biogas $H_2S$ concentration. The experiment also made it possible to verify whether $O_2$ affects the microbiological balance or reduces the performance of the bioreactor.

Two 40 L bioreactors, each containing 20 L of sludge and fed in semi-batch mode with liquid cattle manure at an organic loading rate ranging from 3.36 to 4.05 g COD $L^{-1}$ sludge $d^{-1}$, were operated according to the following sequence:
Day 1: Draining of the supernatant and feeding #1.
Day 2, 3 and 4: Feeding #2, #3 and #4.
Day 5, 6 and 7: Reaction time and decantation time.

The bioreactors were in operation for nine months prior to the start of the experiment and had identical yields. In the present experiment, only bioreactor #31 (BR31) was subjected to microaerobic conditions, and an air flow rate of between 4.0 and 6.3 mL/min was injected into the gas phase of the bioreactor. Bioreactor #30 (BR30) was operated under the same conditions and fed with exactly the same substrate at the same loading rate, but did not receive any air injection in the gas phase. It therefore served as the control for this experiment.

The gas phase was analyzed with a Carle 400 AGC gas chromatograph ($CH_4$, $CO_2$, $N_2$ and $H_2S$) three to five times a week. Colorimetric tubes were used to measure lower $H_2S$ concentrations (Kitagawa, Model 8014-120SM, range: 50-2000 ppm). TS and volatile solids (VS) were measured according to the standard method (APHA 1992). The $O_2$ concentration was measured with a Critical Environment electrochemical probe (MAC-E002, range: 0-25%, accuracy: 0.4%). Total chemical $O_2$ demand (TCOD) was measured on the fed substrate, as well as on the effluent. The volume of gas produced was measured daily using a positive displacement meter, calibrated weekly.

Example II

Pilot AD Bioreactors Unit Experiment

Two bubble columns (BF1, 100; and BF2, 110) (FIG. 13) were operated in parallel and were the core of the pilot unit (FIG. 14). These are two identical cylindrical tanks with hydraulic capacity of 450 L each (height: 1.52 m, 118; width: 0.61 m, 114). The walls are made of stainless steel with a removable Plexiglas cover. Threaded ports are available for external tubing connections. Internal threaded ports allow the installation of diffusers at the lower part of the bubble column. A drain valve (5.08 cm) is available at the lowest point of the conical bottom of the reservoir and allows emptying it completely (160, 162). The biogas tubing is made of transparent reinforced flexible PVC and of rigid threaded PVC (mainly 1.27 cm in diameter). Gas leaks overall check is performed on the system on a regular basis using soap and water.

The bubble column #1 (BF1, 100) is inoculated with 255 L of liquid sludge. Three diffusers 122 of 25.4 cm in diameter are installed at the base of the BF1 column 100. The bubble column #2 (BF2, 110) is equipped with a concentric inner tube (diameter: 30.48 cm, 116) with a single diffuser 126 identical to the one described for bubble column #1 100. The diffuser 126 is located 5 cm from the base of the inner tube. The fluid level is 5 cm lower than the upper part of the tube. This configuration has a lower diameter/height ratio compared to column #1 100. The bubble columns #2, 110, globally contain 361 L of sludge. The volume of sludge used to calculate the conversion rate is 125 L. considering only the liquid inside the inner tube and the liquid below the diffuser. The liquid surrounding the inner tube is considered as stagnant and not participating to the biological process.

A fraction of the biogas produced by a digester at Péloquin farm was diverted from its usual usage and pumped to the diffusers 122, 126, at the base of each bubble column 100, 110 (positive displacement pump: ADI, model R181-FT-EA1; 0.9 $m^3$ @5 psi) (see FIG. 14). A chemical pre-treatment 134 for biogas desulphurization (Sulfatreat 410 HP) was used to control $H_2S$ concentration at bubble column inlet. This helps for the performance evaluation and also keep concentration below the maximum measurement range of the gas analyser used. The manual adjustment of a needle valve allows the biogas to by-pass entirely or partially the chemical pre-treatment 134. The two bubble columns 100, 110 were simultaneously subjected to the same concentration of $H_2S$. Air is injected into the biogas line before it reached the bubble column 100, 110 (peristaltic pump: Cole-Parmer, model RK-74207-00; 0-40 L/h). The air flow was measured and controlled independently for each bubble column 100, 110 with two thermal mass flow controllers 140, 142 (Aalborg, model—GFC17A-VDADL2-BAO; 0-20 L/h). The air/biogas mix flow was measured and manually controlled at the inlet 138, of each bubble column with a rotameter (Dwyer, model DR204282; 0-450 L/h). The total flow at the outlet 144, 146 was measured and logged in real time with a mass flowmeter 148, 150 (Aalborg, model GFM17A-VDADL2-BAO; 0-300 L/h). A drying filter coupled with a chemical filter is installed upstream of the flowmeter 148, 150 to protect the equipment against corrosion. The two mass flowmeters 148, 150 were factory calibrated with a gas composition close to what has been observed during the essays (65% $CH_4$, 30% $CO_2$, 5% air). Air flow injected at inlet and air/biogas flow at the outlet are recorded once per minute (model HOBO U12-006).

The sludge was collected at the end of a digestion cycle by pumping from a pipe located at the bottom of the bioreactor. Prior to inoculate the bubble columns, the sludge has been concentrated two times. The sludge was settled for 24 hours and then, half of the total volume was flushed trough a valve located at the middle height of the liquid column. After draining the supernatant a first time, the reservoir is filled again, following by the settling and the flushing step, repeated one more time. Concentrated sludge is pumped into the bubble columns 100, 110 and biogas starts to be supplied in the diffusers 122, 126 from day #1.

Biogas composition was measured (inlet 136; and outlet 144, 146) by a technician at least once per hour during the course of a daily monitoring. A multi-gas analyser is used (Sewerin, *Multitec* 540) with the following main characteristics:

Methane ($CH_4$, infrared sensor, range 0-100% vol., error$^{+/-}$ 1.5% vol.)

Carbone dioxide ($CO_2$, infrared sensor, range 0-100% vol., measuring error+/−1.5% vol.)

Oxygen ($O_2$, electrochemical sensor, range 0-25%, error+/−3% vol.)

Hydrogen sulphide ($H_2S$, electrochemical sensor, range 0-2000 ppm, if >1000 ppm error+/−100 ppm and if <1000 ppm error+/−6 ppm).

Colorimetric tubes were used periodically to validate analyser's measurement (Kitagawa, model #94-120 SM, range 0.5-1.2% and model #94-120SF, range 50-2000 ppm). Other comparison spot checks were made with a gas chromatograph (GC) in operation at the laboratories of Agriculture and Agri-Food Canada, Sherbrooke, Canada.

The pH and the sludge temperature were manually measured on a regular basis with a sludge sample (Oakon pHTestr30). Room temperature was monitored and controlled.

The performance of the biotransformation process was evaluated according to the following process parameters:

1) $H_2S$ outlet concentration: establishes the level of biogas corrosiveness in regards to its usage as a fuel. $H_2S$ concentration in the biogas prior to combustion will be subject to a provincial regulation in the near future in Quebec.

2) The percentage of reduction of $H_2S$ concentration: gives an indication of performance in regards to $H_2S$ concentration reduction relatively to inlet concentration. Air addition dilutes the gas at the outlet and impacts this parameter, that is calculated as follow:

$$\% \text{ of reduction} = \frac{[H_2S]_{inlet} - [H_2S]_{outlet}}{[H_2S]_{inlet}} \times 100$$

3) Conversion rate of $H_2S$: gives an indication of performance in regards of the volume of sludge experimented, the gas flow bubbled and the biogas concentration difference between inlet and outlet. Calculated as follow:

$$\text{Conversion rate (mg } H_2S/L/h) = \left[\left((Qbiogas_{outlet} - QAir) \times \frac{[H2S]_{inlet(ppm)}}{1000000}\right) - \left(Qbiogas_{outlet} * \frac{[H2S]_{outlet(ppm)}}{1000000}\right)\right] \times \frac{1450 \text{ mg\_H}_2\text{S}}{\text{L\_H}_2\text{S}} \times \frac{1}{V_{sludge}}$$

The results were compiled and calculated from manual measurement. The biogas produced on this farm presented significant variation in $H_2S$ concentration throughout the digestion cycle (2000 to 5000 ppm). The technician readjusted slightly the chemical pre-treatment 134 to stabilize $H_2S$ concentration at inlet 136, 138. Each daily performance presented hereinbelow was the average of the last results of the day (3 to 4 measurements), when the system was considered to be in a steady state regime.

TABLE 3

Results recorded in BF1

| Day* | Average biogas flow rate (L/h) | Average air flow rate (L/h) | Conc. $H_2S$ (ppm) Inlet | Conc. $H_2S$ (ppm) Outlet | Conc. $CH_4$ (%) Inlet | Conc. $CH_4$ (%) Outlet | Conc. $O_2$ outlet (%) | Temperature (° C.) | pH |
|---|---|---|---|---|---|---|---|---|---|
| 14 | 282 | 13.0 | 1900 | 1320 | 66.6 | 66.4 | 1.1 | 26.1 | 8.2 |
| 15 | 287 | 12.0 | 1900 | 1366 | 68.6 | 65.6 | 1.0 |  | 8.3 |
| 16 | 276 | 12.3 | 1900 | 967 | 70.0 | 67.6 | 1.0 | 25.1 |  |
| 19 | 277 | 12.1 | 1900 | 600 | 72.3 | 70.5 | 1.0 | 25.1 | 8.2 |
| 20 | 287 | 12.1 | 1900 | 538 | 72.8 | 69.2 | 1.0 |  |  |
| 21 | 186 | 9.7 | 1900 | 183 | 70.0 | 68.0 | 1.0 | 22.4 | 8.3 |
| 22 | 190 | 9.3 | 1900 | 211 | 70.0 | 67.5 | 1.0 |  | 8.2 |
| 23 | 154 | 6.1 | 1900 | 133 | 65.0 | 65.0 | 1.0 | 23.1 |  |
| 26 | 167 | 8.7 | 1900 | 385 | 72.0 | 68.0 | 1.0 | 23.8 | 8.2 |
| 28 | 163 | 7.8 | 1900 | 240 | 68.5 | 66.0 | 1.0 |  |  |
| 35 | 141 | 7.3 | 1000 | 80 | 65.9 | 63.4 | 1.0 |  | 8.3 |
| 36 | 143 | 7.2 | 1900 | 152 | 65.3 | 64.3 | 1.1 | 24.3 | 8.3 |
| 41 | 138 | 7.3 | 900 | 796 | 67.4 | 64.0 | 1.2 |  |  |
| 42 | 148 | 7.4 | 1000 | 91.6 | 66.0 | 63.2 | 1.1 |  |  |

*Day #1 represents the starting day of biogas bubbling through that sludge

TABLE 4

Results recorded in BF2

| Day* | Average biogas flow rate (L/h) | Average air flow rate (L/h) | Conc. $H_2S$ (ppm) Inlet | Conc. $H_2S$ (ppm) Outlet | Conc. $CH_4$ (%) Inlet | Conc. $CH_4$ (%) Outlet | Conc. $O_2$ outlet (%) | Temperature (° C.) | pH |
|---|---|---|---|---|---|---|---|---|---|
| 14 | 185.9 | 9.0 | 1900 | 830 | 66.6 | 65.0 | 1.2 | 25 | 8.2 |
| 15 | 96.1 | 5.4 | 1900 | 279 | 68.6 | 66.0 | 1.0 | 24.7 | 8.3 |
| 16 | 96.4 | 5.6 | 1900 | 190 | 70.0 | 67.0 | 1.0 | | |
| 19 | 68.7 | 4.3 | 1900 | 250 | 72.3 | 68.8 | 1.0 | 25.1 | 8.2 |
| 20 | 48.5 | 2.7 | 1900 | 187.5 | 72.8 | 69.3 | 1.0 | | |
| 21 | 48.3 | 2.7 | 1900 | 32 | 70.0 | 68.7 | 1.0 | 24.7 | 8.3 |
| 22 | 46.2 | 2.8 | 1900 | 42.5 | 70.0 | 67.3 | 1.0 | 24.7 | 8.2 |
| 23 | 47.6 | 2.8 | 1900 | 35 | 65.0 | 66.3 | 1.0 | | |
| 26 | 44.2 | 3.3 | 1900 | 177 | 72.0 | 68.5 | 1.0 | 22 | 8.2 |
| 28 | 45.2 | 3.0 | 1900 | 50 | 68.5 | 65.3 | 1.0 | | |
| 35 | 46.1 | 2.9 | 1000 | 16 | 65.9 | 64.2 | 1.0 | 22.3 | 8.3 |
| 36 | 43.4 | 3.8 | 1900 | 53 | 65.3 | 62.3 | 0.9 | 23.7 | 8.3 |
| 41 | 44.5 | 3.0 | 900 | 140 | 67.4 | 64.4 | 0.9 | | |
| 42 | 51.9 | 4.0 | 1000 | 95.6 | 66.0 | 63.2 | 0.9 | | |
| 44 | 44.5 | 4.0 | 5000 | 295 | ** | 62.7 | 0.9 | | |
| 47 | 45.5 | 4.1 | 4500 | 340 | ** | 68.3 | 0.8 | | |
| 48 | 43.0 | 4.1 | 4000 | 263 | ** | 63.5 | 0.8 | | |

** No results: Out of the analyser's range for $H_2S$ (>2000 ppm).

Figure 15:
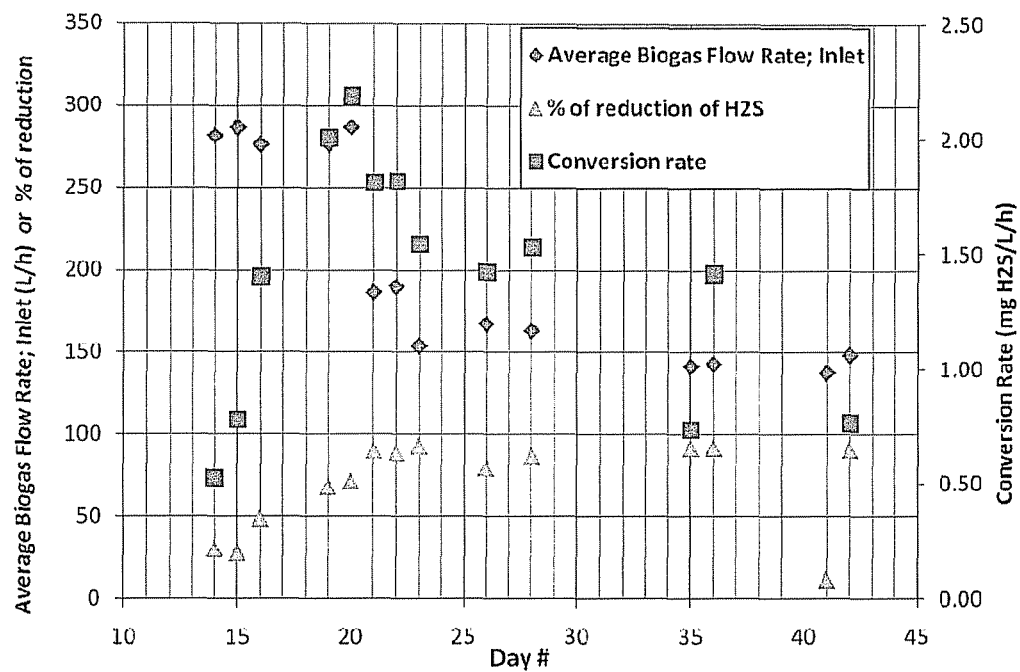
FIG. 15 illustrates the performance measured of one of the bubble column configuration (BF1, 100).

Table 5 and FIG. 15 presents performance for bubble column #1 100. The flow of biogas supplied to the column has been decreased between days #14 to #21 to get an acceptable outlet of $H_2S$ concentration (<300 ppm). Between days #21 to #28, while operating parameters were not changed, the conversion rate was at an average of 1.62 mg $H_2S$/L/h, for a % of reduction of 88%. The drop in conversion rate for days #35, 41 and 42 was due to the fact that the concentration at the inlet 136 was lowered to 1000 ppm.

TABLE 5

Performance recorded for BF1

| Day # | Average biogas flow rate (L/h) | Average biogas flow rate; Outlet (air + biogas) (L/h) | Conc. H2S (ppm) Inlet | Conc. H2S (ppm) Outlet | Conversion rate (mg H2S/L/h) | % of reduction |
|---|---|---|---|---|---|---|
| 14 | 282 | 295 | 1900 | 1320 | 0.52 | 31 |
| 15 | 287 | 299 | 1900 | 1366 | 0.78 | 28 |
| 16 | 276 | 289 | 1900 | 967 | 1.40 | 49 |
| 19 | 277 | 289 | 1900 | 600 | 2.00 | 68 |
| 20 | 287 | 299 | 1900 | 538 | 2.18 | 72 |
| 21 | 186 | 196 | 1900 | 183 | 1.81 | 90 |
| 22 | 190 | 199 | 1900 | 211 | 1.81 | 89 |
| 23 | 154 | 160 | 1900 | 133 | 1.54 | 93 |
| 26 | 167 | 176 | 1900 | 385 | 1.42 | 80 |
| 28 | 163 | 171 | 1900 | 240 | 1.53 | 87 |
| 35 | 141 | 149 | 1000 | 80 | 0.74 | 92 |
| 36 | 143 | 150 | 1900 | 152 | 1.41 | 92 |
| 41 | 138 | 145 | 900 | 796 | * | 12 |
| 42 | 148 | 156 | 1000 | 92 | 0.76 | 91 |

*Result unavailable

Figure 16:
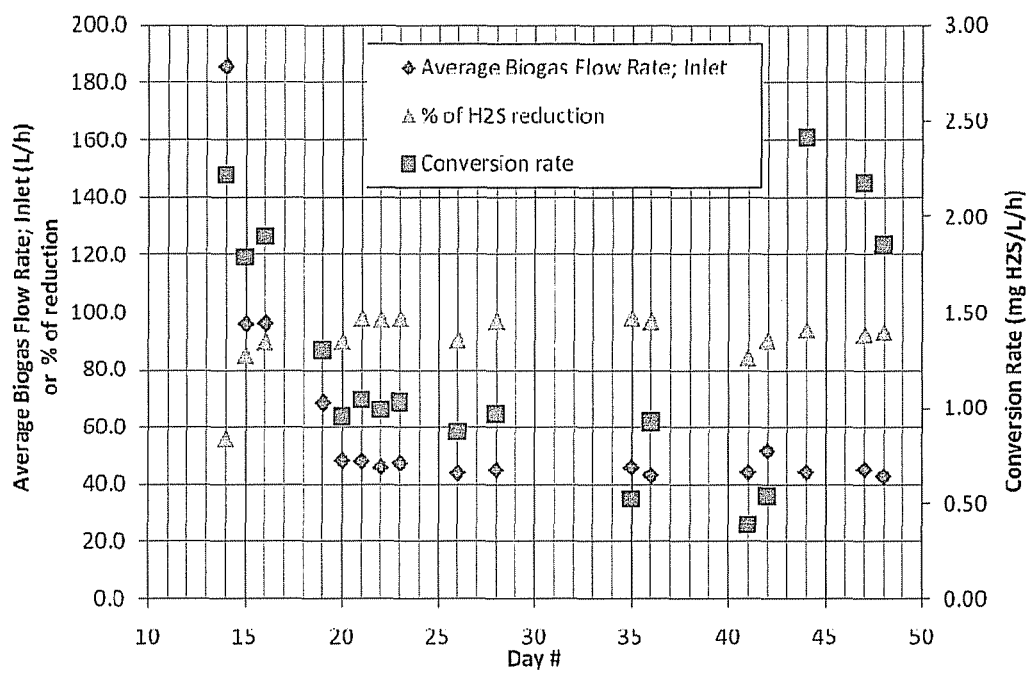
FIG. 16 illustrates the performance measured of the second bubble column configuration (BF2, 110).

Table 6 and FIG. 16 presents the performance of bubble column #2 110. Biogas flow rate supplied to the column 110 has been decreased between days #14 to 19 to get to an acceptable $H_2S$ concentration at the outlet 146 (<300 ppm). Between days #20 and 28, while operating parameters were not changed, the average conversion rate was 0.98 mg $H_2S$/L/h, for an average % of reduction of 95%. The drop in conversion rate for days #35, 41 and 42 (average of 0.48 mg $H_2S$/L/h) was mainly due to the fact that the inlet 136 concentration has been decreased to 1000 ppm. High concentrations applied to the input between days #44 and 48 (between 4000 and 5000 ppm) offered the best performance in terms of conversion rate with an average of 2.15 mg $H_2S$/L/h, for a percentage of reduction of $H_2S$ of 93%. During that period (day #44 to 48), oxygen concentration at the outlet 146 decreased from 0.9 to 0.8% (Table 4). Using stoichiometric equation for day 48, 0.084 L/h of oxygen was required to oxidize the mass of sulphur that was assumed to be biotransformed. This represents 10% of the oxygen supplied for that day. The reduction of the oxygen at the outlet 146 was due to the high conversion rate of $H_2S$.

TABLE 6

Performance recorded for BF2

| Day # | Average biogas flow rate (L/h) | Average biogas flow rate; Outlet (air + biogas) (L/h) | Conc. H2S (ppm) Inlet | Conc. H2S (ppm) Outlet | Conversion rate (mg H2S/L/h) | % of reduction |
|---|---|---|---|---|---|---|
| 14 | 185.9 | 195 | 1900 | 830 | 2.22 | 56 |
| 15 | 96.1 | 102 | 1900 | 279 | 1.79 | 85 |
| 16 | 96.4 | 102 | 1900 | 190 | 1.90 | 90 |
| 19 | 68.7 | 73 | 1900 | 250 | 1.30 | 87 |
| 20 | 48.5 | 51 | 1900 | 188 | 0.96 | 90 |
| 21 | 48.3 | 51 | 1900 | 32 | 1.05 | 98 |
| 22 | 46.2 | 49 | 1900 | 43 | 0.99 | 98 |
| 23 | 47.6 | 50 | 1900 | 35 | 1.03 | 98 |
| 26 | 44.2 | 47 | 1900 | 177 | 0.88 | 91 |
| 28 | 45.2 | 48 | 1900 | 50 | 0.97 | 97 |
| 35 | 46.1 | 49 | 1000 | 16 | 0.53 | 98 |
| 36 | 43.4 | 47 | 1900 | 53 | 0.93 | 97 |
| 41 | 44.5 | 48 | 900 | 140 | 0.39 | 84 |
| 42 | 51.9 | 56 | 1000 | 96 | 0.54 | 90 |
| 44 | 44.5 | 48 | 5000 | 295 | 2.41 | 94 |
| 47 | 45.5 | 50 | 4500 | 340 | 2.18 | 92 |
| 48 | 43.0 | 47 | 4000 | 263 | 1.85 | 93 |

While the description has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth, and as follows in the scope of the appended claims.

What is claimed is:

1. A process for reducing hydrogen sulphide concentration in a biogas comprising the steps of:
   a) supplying air in a psychrophilic anaerobic bioreactor producing biogas, the bioreactor comprising a gas phase, and a liquid phase containing an anaerobic sludge, and
   b) removing hydrogen sulphide from biogas under psychrophilic conditions by oxidation to elemental sulphur.

2. A process for reducing hydrogen sulphide concentration in a biogas comprising the steps of:
   a) supplying air in a psychrophilic anaerobic bioreactor producing biogas, the bioreactor comprising a gas phase, and a liquid phase containing an anaerobic sludge, and
   b) removing the converted sulphur from the hydrogen sulphide from the bioreactor.

3. The process of claim 1 or 2, wherein additional biogas is supplied from at least one adjacent bioreactor connected to the psychrophilic bioreactor.

4. The process of claim 3, further comprising the step of feeding the psychrophilic bioreactor with an organic substrate.

5. The process of claim 4, wherein the organic substrate is a liquid substrate, a semi-liquid substrate or a solid substrate.

6. The process of claim 5, wherein the organic substrate is a live-stock waste, an agricultural waste, a municipal waste, an agri-food waste, an industrial organic waste, or a mixture thereof.

7. The process of claim 6, wherein the live-stock waste is an animal waste.

8. The process of claim 7, wherein the animal waste is a cattle manure, a pig manure, a poultry manure, or a mixture thereof.

9. The process of claim 1 or 2, wherein the psychrophilic bioreactor is at a temperature between 5° C. to 30° C.

10. The process of claim 1 or 2, wherein the biogas is mixed with air.

11. The process of claim 10, wherein the biogas-air mixture is bubbled into the liquid phase of the psychrophilic bioreactor.

12. The process of claim 1 or 2, wherein the flow rate of injected air is between 2 to 20% of the flow rate of biogas.

13. A process for reducing hydrogen sulphide concentration in a biogas comprising the steps of:
   a) supplying a first psychrophilic bioreactor with air and biogas, the biogas provided from a second bioreactor, the first psychrophilic bioreactor comprising a sludge; and
   b) removing hydrogen sulphide from biogas by oxidation to elemental sulphur.

14. A process for reducing hydrogen sulphide concentration in a biogas comprising the steps of:
   a) supplying a first psychrophilic bioreactor with air and biogas, the biogas provided from a second bioreactor, the first psychrophilic bioreactor comprising a sludge; and
   b) removing the converted sulphur from the hydrogen sulphide from the first bioreactor.

15. The process of claim 13 or 14, wherein the first psychrophilic bioreactor comprises a gas phase.

16. The process of process of claim 15, wherein the first psychrophilic bioreactor further comprises a liquid phase.

17. The process of claim 16, wherein the sludge is contained in the liquid or gas phase of the first bioreactor.

18. The process of claim 13 or 14, further comprising the step of inoculating the first psychrophilic bioreactor with a sludge collected from a second psychrophilic bioreactor.

19. The process of claim 18, wherein the sludge has been acclimated to a solid or a liquid organic substrate.

20. The process of claim 19, wherein the organic substrate is a live-stock waste, an agricultural waste, a municipal waste, an agri-food waste, an industrial organic waste, or a mixture thereof.

21. The process of claim 20, wherein the live-stock waste is an animal waste.

22. The process of claim 21, wherein the animal waste is a cattle manure, a pig manure, a poultry manure, or a mixture thereof.

23. The process of claim 13 or 14, wherein the first psychrophilic bioreactor is at a temperature between 5° C. to 30° C.

24. The process of claim 13 or 14, wherein the biogas is mixed with air.

25. The process of claim 24, wherein the biogas-air mixture is bubbled into the first psychrophilic bioreactor.

26. The process of claim 13 or 14, wherein the flow rate of injected air is between 2 to 20% of the flow rate of biogas produced by the second bioreactor.

* * * * *